US011628141B2

(12) United States Patent
Hoffmann et al.

(10) Patent No.: US 11,628,141 B2
(45) Date of Patent: Apr. 18, 2023

(54) METHOD FOR PRODUCING AN, IN PARTICULAR ORAL, ACTIVE SUBSTANCE LAMINATE, AND ACTIVE SUBSTANCE LAMINATE, IN PARTICULAR ORAL ACTIVE SUBSTANCE LAMINATE

(71) Applicant: LTS LOHMANN THERAPIE-SYSTEME AG, Andernach (DE)

(72) Inventors: Michael Hoffmann, Neuwied (DE); Elvira Kirstgen, Neuwied (DE); Ralf-Ingo Stein, Dierdorf (DE); Sandra Wiedersberg, Steigra (DE); Thomas Stumper, Bad Honningen (DE)

(73) Assignee: LTS LOHMANN THERAPIE-SYSTEME AG, Andernach (DE)

(*) Notice: Subject to any disclaimer, the term of this patent is extended or adjusted under 35 U.S.C. 154(b) by 386 days.

(21) Appl. No.: 16/603,021

(22) PCT Filed: Apr. 5, 2018

(86) PCT No.: PCT/EP2018/058761
§ 371 (c)(1),
(2) Date: Oct. 4, 2019

(87) PCT Pub. No.: WO2018/185238
PCT Pub. Date: Oct. 11, 2018

(65) Prior Publication Data
US 2020/0030233 A1 Jan. 30, 2020

(30) Foreign Application Priority Data

Apr. 6, 2017 (DE) .................. 10 2017 107 468.6

(51) Int. Cl.
*A61K 9/00* (2006.01)
*A61K 9/16* (2006.01)
*A61K 9/70* (2006.01)
A61K 47/38 (2006.01)
A61F 13/00 (2006.01)

(52) U.S. Cl.
CPC ............ *A61K 9/0056* (2013.01); *A61K 9/006* (2013.01); *A61F 2013/00646* (2013.01); *A61K 9/1694* (2013.01); *A61K 9/7007* (2013.01); *A61K 47/38* (2013.01)

(58) Field of Classification Search
None
See application file for complete search history.

(56) References Cited

U.S. PATENT DOCUMENTS

2003/0107149 A1* 6/2003 Yang .................... A61K 9/7015
264/134
2011/0274795 A1 11/2011 Bogue et al.
2015/0217322 A1* 8/2015 Rooijmans ................ B05C 1/08
118/200

FOREIGN PATENT DOCUMENTS

| DE | 19826592 A1 | 12/1999 | |
|---|---|---|---|
| DE | 202008017304 U1 * | 10/2009 | ......... A61K 31/7048 |
| DE | 202008017304 U1 | 10/2009 | |
| EP | 1087759 B1 | 8/2002 | |
| EP | 2564938 A1 | 3/2013 | |
| JP | 63037304 A | 2/1988 | |
| JP | 2005342154 A | 12/2005 | |
| WO | 2003011248 A1 | 2/2003 | |
| WO | 2003018071 A1 | 3/2003 | |
| WO | 2012053006 A2 | 4/2012 | |
| WO | 2016094567 A1 | 6/2016 | |

OTHER PUBLICATIONS

Office Action for Japanese Application No. 2019-554467, dated Jun. 29, 2021, 6 pages.

* cited by examiner

*Primary Examiner* — Bong-Sook Baek
(74) *Attorney, Agent, or Firm* — Fay Sharpe LLP

(57) ABSTRACT

The invention relates to a method for producing an active substance laminate, especially an oral active substance laminate (100), having at least one active-substance-containing layer (31), which is arranged on a substrate (20), wherein the method comprises the following steps:
a) providing a substrate (20) having an upper side (21) and an underside (22);
b) applying an active-substance-containing mass (24) in a gap (25) formed by a first rotating roller (26) and a second rotating roller (27);
c) transporting the substrate (20) to the second roller (27) by means of a third rotating roller (28) in such a way that the active-substance-containing mass (24) is applied to the upper side (21) of the substrate (20) by the second roller (27) in the form of an active-substance-containing layer (31);
d) transporting an intermediate laminate (30), formed by the substrate (20) and the active-substance-containing layer (31), to a drying device (40); and
e) drying the intermediate laminate (30), especially the active-substance-containing layer (31).

9 Claims, 3 Drawing Sheets

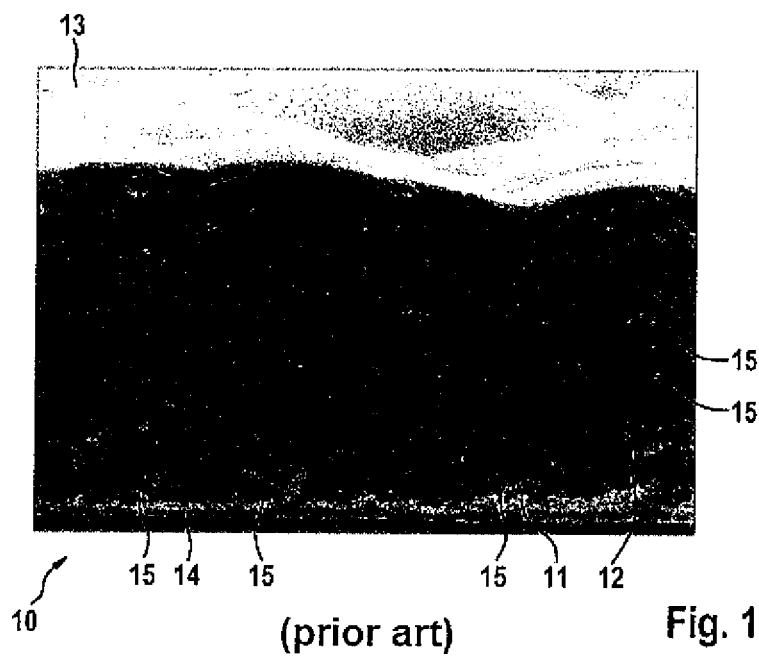
(prior art) Fig. 1
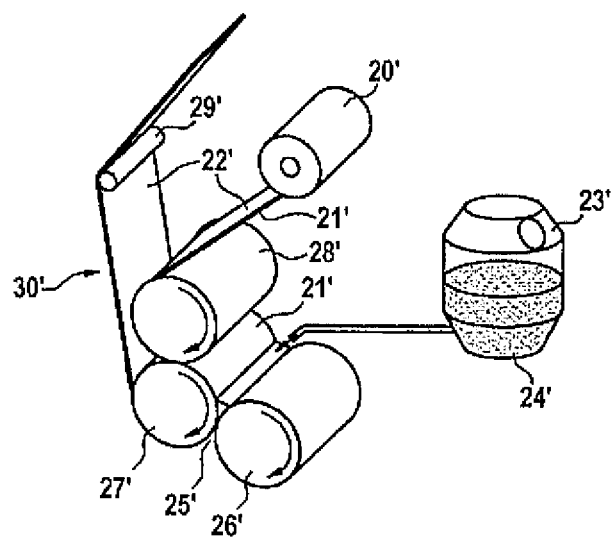
(prior art) Fig. 2

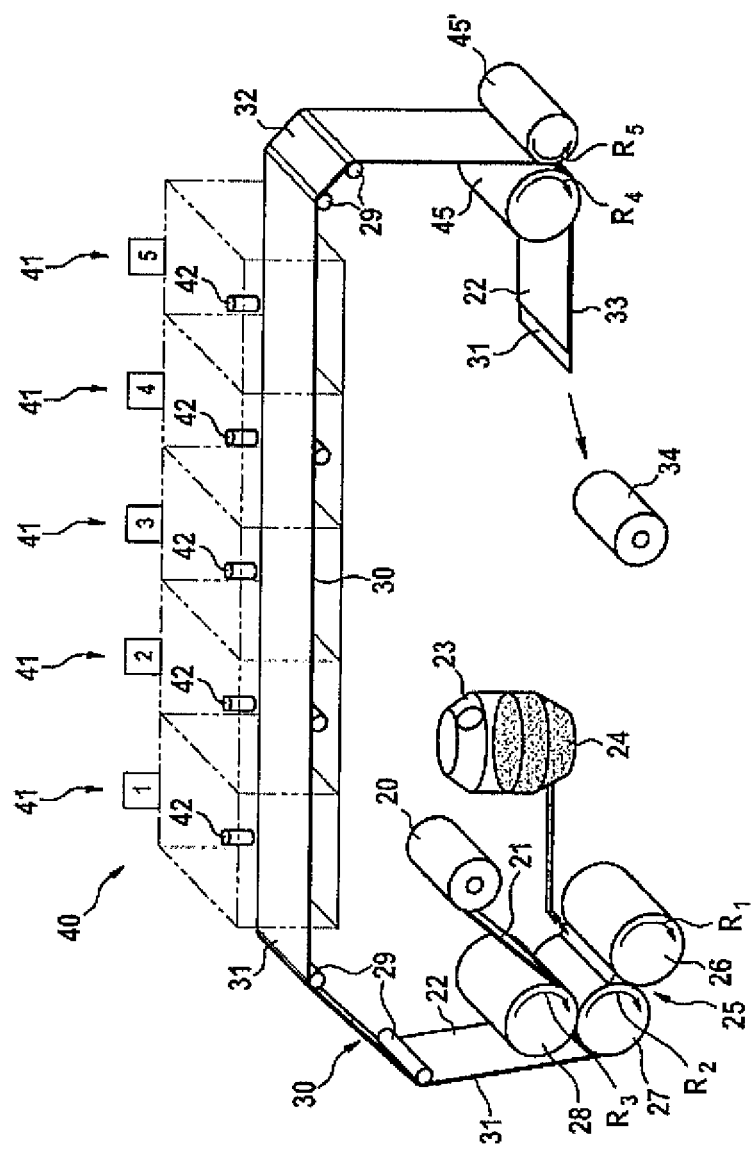

METHOD FOR PRODUCING AN, IN PARTICULAR ORAL, ACTIVE SUBSTANCE LAMINATE, AND ACTIVE SUBSTANCE LAMINATE, IN PARTICULAR ORAL ACTIVE SUBSTANCE LAMINATE

The invention relates to a method for producing an, especially oral, active substance laminate, having at least one active-substance-containing layer, which is arranged on a substrate, according to claim 1.

Oral active substance laminates or oral active substance films (oral thin films) are thin, active-substance-containing films which are put directly in the mouth or are placed against the oral mucosa and dissolve there within a short space of time. Dissolution times are, for example, between one minute and thirty minutes. In the case of transmucosal films the active substance passes into the bloodstream via the oral mucosa, without having to pass through the gastro-intestinal tract.

Oral active substance laminates or active substance films are thin, flexible pharmaceutical excepients. They are placed, for example, on or beneath the tongue and melt there. In addition, it is possible to adhere the oral thin films to the oral mucosa, especially to the inside of the buccal cavity. The very good blood flow in the oral mucosa ensures a direct transfer of the active substance into the bloodstream.

It is also known to provide dental prophylaxis treatments and/or mouth-freshening products in the form of oral active substance laminates.

FIG. 1 shows an example of a prophylaxis laminate of this kind. In this case it is a product 10 approximately 70 μm thick, wherein menthol is incorporated in the form of oil droplets 15 in a matrix 12. The surface 13 of the product 10 is extremely uneven, as can be clearly seen. This is the result of the previously known production method for oral active substance laminates. The underside 14, by contrast, is very smooth or flat, wherein this smooth or flat design of the underside 14 may be attributed to the used carrier film 11. Although the same amount of active substance is contained per area unit, the matrix 12 is nevertheless relatively inhomogeneous in cross-section. It can be seen that more droplets 15 are formed in the direction of the carrier film 11, wherein these droplets have a smaller diameter than the droplets 15 that are formed in the region of the surface 13.

The two most important techniques that are used to produce the oral films are solvent casting and melt extrusion.

Previous methods for producing oral active substance laminates furthermore cause the problem that the areal density of active-substance-containing layers, especially in multi-layer systems, is not sufficiently constant. An exemplary known method is standard roll coating. The areal density of an active-substance-containing layer usually cannot be determined separately, but only in association, i.e. summed, with the active-substance-free layers. The total areal density of an oral active substance laminate includes fluctuations in the areal density both of the active-substance-containing layer and of the active-substance-free layer(s).

When applying an active-substance-containing layer by means of standard roll coating, the active-substance-containing mass to be coated is applied to an active-substance-free layer or to a layer that likewise is an active-substance-containing layer, or rather to an active-substance-free substrate or active-substance-containing substrate. Fluctuations in respect of the thickness of the substrate or in respect of the areal density of the substrate or the active-substance-free or active-substance-containing layer may thus have a direct effect on the fluctuations in the entire oral active-substance laminate.

In EP 1 087 759 B1 what is known as a "liquid-on-liquid" coating is described. In that case, multi-layer laminates may be created in a closed sequence of extremely economical production processes. Firstly, a first mass that is flowable under processing conditions is applied as first layer, and then a further mass that is flowable under processing conditions is applied as further layer.

FIG. 2 shows an exemplary standard coating method. A rolled-up substrate material 20' is unrolled with the aid of a, optionally rubberised, transport roller 28' and is guided into a gap 25' formed by a first roller 26' and a second roller 27'. The active-substance-containing mass 24' is applied to the upper side 21' of the substrate 20' in the region of the gap 25'. The active-substance-containing mass 24' is applied directly to the upper side 21'. The active substance 24' therefore does not come into contact with the surface of the second roller 27'. With the aid of the second roller 27', the coated substrate 20' is guided, together with the applied active-substance-containing mass 24', as intermediate laminate 30', for example to a further transport roller 29'. Fluctuations in respect of the areal density of the substrate 20' thus have a direct effect in the form of fluctuations in the intermediate laminate 30' or in the entire oral active substance laminate.

The aim of the present invention is therefore to describe a method for producing an, especially oral, active substance laminate in which an active-substance-containing layer may be produced or applied independently of the areal density or the layer thicknesses or layer thickness fluctuations of the substrate.

In accordance with the invention the explained aim is achieved in respect of the method for producing an, especially oral, active substance laminate by the subject matter of claim 1.

The invention is based on the idea of describing a method for producing an, especially oral, active substance laminate, having at least one active-substance-containing layer, which is arranged on a substrate. The method according to the invention comprises the following steps:

a) providing a substrate having an upper side and an underside;

b) applying an active-substance-containing mass in a gap formed by a first rotating roller and a second rotating roller;

c) transporting the substrate to the second roller by means of a third rotating roller in such a way that the active-substance-containing mass is applied to the upper side of the substrate by the second roller in the form of an active-substance-containing layer;

d) transporting an intermediate laminate, formed by the substrate and the active-substance-containing layer, to a drying device; and e) drying the intermediate laminate, especially the active-substance-containing layer.

The active-substance-containing mass in accordance with the invention is applied with a constant thickness or a constant areal density and independently of the substrate to the upper side of the substrate by the second roller so as to form an active-substance-containing layer.

The first and the second roller are preferably arranged next to one another so that a gap may be formed in the vertical direction between the two rollers, into which gap an active-substance-containing mass may be applied. In other words the active-substance-containing mass is filled into the gap for example starting from a container that is filled with the active-substance-containing mass. The active-substance-containing mass is transported along the second roller downwardly in the vertical direction. In order to ensure transport of this kind, it is possible for example to provide a scraper or a doctor blade on the first roller so that the active-substance-containing mass is transported downwardly only along the second roller.

A third roller is arranged above or beneath the second roller. A substrate is transported to the second roller by means of said third rotating roller. The substrate may be in web form. Furthermore, it is conceivable that the substrate is present in the rolled-up state and is unrolled and transported to the second roller with the aid of the third rotating roller. Since the third rotating roller is arranged above or beneath the second rotating roller, the active substance or the active-substance-containing mass may be applied to the upper side of the substrate by the second roller. The active substance or the active-substance-containing mass is firstly applied with constant thickness to the surface of the second rotating roller and is transported with the aid of the roller surface. The active substance or the active-substance-containing mass therefore is not applied to the substrate directly from a container, but indirectly by pressing the active substance located on the roller surface onto the upper side of the substrate.

The active substance is preferably present in dissolved form in the active-substance containing mass. The active-substance-containing mass may be present in the form of an emulsion. It is also possible for the active substance to be present in dispersed form in the active-substance-containing mass.

The active-substance-containing mass preferably comprises a solvent. The solvent ensures the flowablity of the active-substance-containing mass. The solvent is preferably removed in step e), specifically in the drying step. In other words, the intermediate laminate, especially the active-substance-containing layer, is dried by the removal of the solvent. Besides water, other solvents may also be used, for example alcohols such as methanol, ethanol, propanol, or solvent mixtures, for example water-alcohol mixtures.

A substrate is understood to mean a substrate that is coated with sufficient medicinal active substance by way of the method according to the invention. It should not be ruled out that the substrate may also contain a proportion of any sort of active substance. The substrate may be free from active substance or may contain active substance. In the simplest case the substrate may consist of cellulose without active substance.

In a preferred embodiment of the invention the substrate has the composition specified in Table 1. The stated amounts are based on the production of 150 kg liquid mass of the substrate to be produced.

TABLE 1

| Constituent | Percentage by weight (w/w) | Amount (kg) |
| --- | --- | --- |
| Purified water | 77.50 | 116.249 |
| Preservative(s) | 0.24 | 0.356 |
| Auxiliary/Auxiliaries | 0.11 | 0.169 |
| Antioxidant | 0.01 | 0.018 |

TABLE 1-continued

| Constituent | Percentage by weight (w/w) | Amount (kg) |
| --- | --- | --- |
| Matrix material(s) | 21.30 | 31.960 |
| Filler(s) | 0.55 | 0.827 |
| Sweetener(s) and flavouring(s) | 0.28 | 0.422 |
| Release Liner[a] | | |
| Total | 100.0 | 150.00 |

[a]constituent that is removed during the production process.

The substrate forms an intermediate laminate together with the applied active substance, i.e. the formed active-substance-containing layer.

The substrate may be connected, especially releasably, on the underside to a carrier film. The carrier film is used for example as a process film, with the aid of which the method according to the invention may be performed in a simplified way. Especially, the transport of the coated substrate or of the intermediate laminate is facilitated with the aid of a carrier film.

The active-substance-free substrate may be formed by two active-substance-free and/or active-substance-containing layers. In this case a first active-substance-free layer forms the upper side of the substrate and a second layer forms the underside of the substrate, for example. It is possible that at least one further active-substance-free or active-substance-containing layer is formed between the first layer and the second layer.

For example, the active substance of the active-substance-containing layer may be naloxone and/or fentanyl.

The active-substance-containing layer may be a mucoadhesive layer. In a preferred embodiment of the invention the active-substance-containing or mucoadhesive layer has the composition specified in Table 2. The stated amounts are based on the production of 65 kg liquid mass of the active-substance-containing or mucoadhesive layer to be produced.

TABLE 2

| Constituent | Percentage by weight (w/w) | Amount (kg) |
| --- | --- | --- |
| Fentanyl citrate | 0.86 | 0.561 |
| Purified water | 88.82 | 57.733 |
| Plasticiser | 0.48 | 0.311 |
| Preservative(s) | 0.18 | 0.117 |
| Colouring agent(s) | 0.01 | 0.008 |
| pH-value modulator(s) | 1.31 | 0.855 |
| Antioxidant | 0.01 | 0.004 |
| Matrix material(s) | 8.32 | 5.411 |
| Total | 100.0 | 65.00 |

The stated matrix materials may be water-soluble polymers or polymers that swell upon contact with water, for example cellulose and/or derivatives thereof.

The first roller, the second roller and the third roller rotate in the same rotation direction. In other words the first, the second and the third roller rotate simultaneously in a clockwise direction or simultaneously in an anticlockwise direction.

The rotation speed of the first rotating roller may be 0.0 m/min-0.5 m/min, especially 0.1 m/min-0.3 m/min. The rotation speed of the first rotating roller preferably has a value within the stated value ranges, the rotation speed remaining constant during the method according to the invention. The rotation speed of the second rotating roller may be 0.8 m/min-2.3 m/min, especially 1.0 m/min-1.5 m/min. The rotation speed of the second rotating roller preferably has a value within the stated value ranges, the rotation speed remaining constant during the method according to the invention. The rotation speed of the third rotating roller may be 0.5 m/min-1.5 m/min, especially 0.7 m/min-1.0 m/min. The rotation speed of the third rotating roller preferably has a value within the stated value ranges, the rotation speed remaining constant during the method according to the invention.

It has been found that at the stated rotation speeds an especially uniform areal density with regard to the active-substance-containing layer may be applied to the substrate, especially to the first active-substance-free layer.

The gap between the first rotating roller and the second rotating roller may have a width of from 0.2 mm-0.9 mm, especially of 0.6 mm. The gap width is preferably constant during the method according to the invention and has a value within the stated value range.

It has been found that an especially uniform coating of the substrate with an active-substance-containing layer is possible with the aid of a gap size of this kind.

The intermediate laminate is transported to a drying device, wherein the intermediate laminate is acted on in the drying device by a temperature of 30° C.-120° C., especially of 60° C.-90° C., especially of 75° C.

The intermediate laminate is preferably transported at a speed, known as the "web speed", of 0.7 m/min-0.9 m/min, especially of 0.8 m/min. The web speed is the process speed. The web speed may also be referred to as the transport speed of the active substance laminate to be produced. This speed is the same during the entire method and has a value within the stated value range.

If the intermediate laminate is acted on by a temperature of this kind, an intermediate laminate may be produced that provides an especially flat or smooth result in respect of the surface formed on the active-substance-containing layer.

The drying device may be, for example, a drying channel. The drying channel may have a plurality of zones, especially a plurality of temperature zones. The drying channel preferably has at least two, especially at least three, especially at least four, especially at least five, especially at least ten, especially at least thirteen drying zones. With an increasing number of drying zones the intermediate laminate may be dried more quickly. With an increasing number of drying zones the method thus may be performed more quickly.

The drying device may have at least one air jet so that the intermediate laminate may be acted on by a temperature of 30° C.-120° C., especially of 60° C.-90° C., especially of 75° C., by heated air.

If the drying device is a drying channel with a plurality of drying zones, the drying device may have a plurality of air jets, wherein the heated air of the air jets generates different temperatures. It may preferably be provided that the intermediate laminate is dried within the drying channel at the start in the drying zones with low temperatures and as it passes further through the drying channel in the drying zones with higher temperatures.

In a further preferred embodiment of the method according to the invention the intermediate laminate is introduced into the drying channel in such a way that the active-substance-containing layer points in the direction of the at least one air jet.

For example, the at least one air jet is arranged above the active-substance-containing layer. The active-substance-containing layer is thus acted on by warm air from above. The active-substance-containing layer is thus acted on directly by a higher temperature than the underside of the substrate.

In an alternative embodiment it is possible that drying devices, especially air jets, are arranged beneath the substrate.

In a further embodiment of the invention the method is furthermore characterised by the step
  f) guiding the dried intermediate laminate through laminating rollers and forming the active substance laminate.

Two laminating rollers rotate preferably in opposite directions or in two different rotation directions. The intermediate laminate is strengthened as a result. The two laminating rollers may also be heated.

The further step
  g) concerns rolling up the dried intermediate laminate, i.e. rolling up the active substance laminate.

In rolled-up form the active substance laminate may be transported to a further device. It is furthermore possible that the rolled-up, dried active substance laminate is used in another operating facility.

In one embodiment of the invention further method steps may be performed, specifically
  h) unrolling the active substance laminate;
  i) optionally removing the carrier film; and
  j) dividing the active substance laminate into multiple active substance laminate portions.

Alternatively, it is possible that the carrier film is removed from the active substance laminate already before step g), that is to say before rolling up the active substance laminate. The active substance laminate may be divided into multiple active substance laminate portions for example by cutting and/or punching and/or perforation and subsequent tearing. The individual active substance laminate portions form ready-to-use oral active substance laminates or oral active substance films, which may be packaged.

A constant and precise active substance content in an oral active substance laminate may be produced with the aid of the method according to the invention. Especially it is possible to apply an active-substance-containing layer to an active-substance-free or active-substance-containing substrate with a constant and precise thickness or with a constant and precise areal density.

In principle it should be possible to coat the active-substance-containing layer directly onto a carrier and then to coat the active-substance-free layer or layers on the active-substance-containing layer. A change to the coating order, however, means that the active-substance-containing layer would have to be guided multiple times through the drying channel. The active substance, in some circumstances, cannot withstand the high temperatures, and therefore the previously described order of the method steps is considered to be optimal.

A secondary aspect of the invention concerns an active substance laminate, especially an oral active substance laminate, that is produced especially with the method explained in accordance with the invention, wherein the active substance laminate has at least one active-substance-containing layer, which is arranged on a substrate.

In an especially preferred embodiment of the invention the active substance laminate is an oral active substance laminate.

Synonyms or further terms that describe an oral active substance laminate are, for example, thin-film, oral film, wafer, oral strip, orodispersible film, oral thin film, oral soluble film, dissofilms, buccal soluble film, mucoadhesive film, buccal film and transmucosal film. The oral active substance laminate according to the invention may be formed as one of the described films/laminates.

The active-substance-containing layer forms at least one of the two outer surfaces of the oral active substance laminate. The substrate may be free from active substance or may contain active substance.

An active-substance-free substrate is understood to mean a substrate that is only coated with sufficient medicinal active substance by way of the method according to the invention. It should not be ruled out that the substrate may also contain a proportion of any kind of active substance.

In accordance with the invention the active-substance-containing layer has a constant areal density independently of the thickness and/or the areal density of the substrate.

The active substance may be a pharmaceutical active substance, especially an analgesic, especially fentanyl and/or buprenorphine and/or opioid antagonist. An opioid antagonist may preferably be naloxone. Buprenorphine is preferably present in the form of a salt or base.

The active-substance-containing layer may have an areal density of 40 $g/m^2$-100 $g/m^2$, especially of 50 $g/m^2$-70 $g/m^2$, especially of 55 $g/m^2$-65 $g/m^2$, especially of 60 $g/m^2$.

The substrate is formed for example from one layer. The substrate is preferably formed from at least two layers. The at least two layers may be active-substance-free and/or active-substance-containing layers.

The substrate and/or at least one, especially active-substance-free, layer of the substrate may consist of a polymer and/or a material that swells upon contact with water and/or a water-soluble material. Reference is made to Table 1 with regard to a preferred composition of the substrate.

The, especially active-substance-free, substrate may have an areal density of 100 $g/m^2$-300 $g/m^2$, especially of 240 $g/m^2$-280 $g/m^2$, especially of 250 $g/m^2$-270 $g/m^2$, especially of 262 $g/m^2$.

The, especially active-substance-free, layers may each have an areal density of 80 $g/m^2$-180 $g/m^2$, especially of 100 $g/m^2$-160 $g/m^2$, especially of 120 $g/m^2$-140 $g/m^2$, especially of 131 $g/m^2$.

A carrier film may be formed on the side of the, especially active-substance-free, substrate opposite the active-substance-containing layer.

At the time of use, the active-substance-containing layer of the active substance laminate or the formed oral thin film adheres to the oral mucosa of the user. The oral thin film in other words adheres on the basis of mucoadhesion. The active substance of the active-substance-containing layer is absorbed by the user through the oral mucosa. Reference is made to Table 2 with regard to a preferred composition of the active-substance-containing layer or a mucoadhesive layer.

The active-substance-containing mass may have a viscosity of 30 dPas-60 dPas, especially of 40 dPas-50 dPas, especially of 45 dPas.

An active-substance-free mass may have a viscosity of 150 dPas-250 dPas, especially of 180 dPas-230 dPas, especially of 200 dPas. The active-substance-free mass may be used to produce an active-substance-free layer of the substrate.

The invention will be explained in greater detail hereinafter on the basis of exemplary embodiments with reference to the accompanying schematic drawings.

In the drawings:

FIG. 1 shows a cross-section through an oral thin film according to the prior art;

FIG. 2 shows a schematic depiction in respect of a coating method known from the prior art;

FIG. 3 shows a schematic depiction in respect of the method according to the invention.

Figure 4:
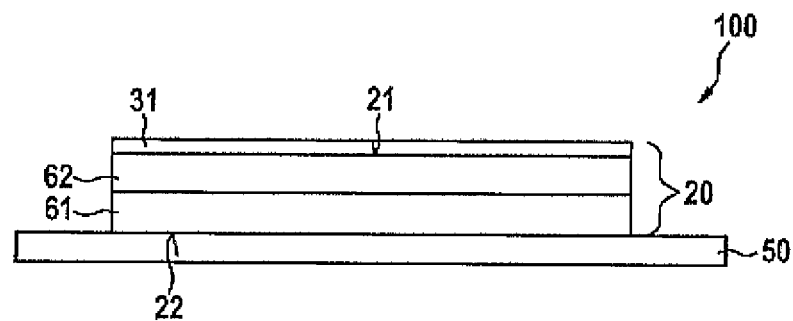
FIG. 4 shows a cross-section through an oral active substance laminate according to the invention.

In the description below, like reference signs are used for like and equivalent parts.

FIG. 3 shows schematically the process of the method according to the invention for producing an oral active substance laminate. Especially the individual stations of the method according to the invention are shown.

A, especially active-substance-free, substrate 20 with an upper side 21 and an underside 22 is provided in rolled-up form. Furthermore, a container 23 can be seen, in which there is situated an active-substance-containing mass 24. The active-substance-containing mass 24 is transported to a gap 25. The gap 25 is formed by a first rotating roller 26 and a second rotating roller 27. The gap 25 between the first rotating roller 26 and the second rotating roller 27 has a width of 0.6 mm, for example.

The first rotating roller 26 and the second rotating roller 27 are arranged approximately next to one another, especially in parallel, in the horizontal direction so that a substantially vertically running gap 25 may be formed. A third rotating roller 28 is arranged vertically above the second rotating roller 27. In an alternative embodiment of the method the third rotating roller 28 may also be situated beneath the second rotating roller 27.

In order to ensure that the active-substance-containing mass 24 is transported along the second roller 27 in the direction of the third roller 28, a doctor blade or scraper (not shown) may be formed on the first rotating roller 26. The substrate 20 is transported to the second rotating roller 27 with the aid of the third rotating roller 28 in such a way that the active substance is applied from the surface of the second roller 27 to the upper side 21 of the substrate 20.

The rotation direction $R_1$ of the first roller 26 and the rotation direction $R_2$ of the second roller 27 and the rotation direction $R_3$ of the third roller 28 coincide. The rotation directions $R_1$, $R_2$ and $R_3$ are thus the same. The rotation speeds in the presented example are for the first roller (26) 0.0 m/min-0.5 m/min, for the second roller (27) 0.8 m/min-2.3 m/min, and for the third roller (28) 0.5 m/min-1.5 m/min. The rotation speeds of the first roller 26, the second roller 27 and the third roller 28 have a value within the stated value ranges, wherein all rotation speeds are constant whilst the method according to the invention is being carried out.

The intermediate laminate 30, which is formed by the substrate 20 and the active-substance-containing layer 31, is transported to a drying device 40 with the aid of transport rollers 29. The drying device 40 is a drying channel, for example with five drying zones 41. Each drying zone has an air jet 42. Different temperatures are available in the five drying zones 41 with the aid of the air jets 42, and so the intermediate laminate 30 is acted on in the different drying zones 41 by different temperatures, which lie between 30° C. and 120° C.

The intermediate laminate 31 is transported in the drying device 40 in such a way that the active-substance-containing layer 31 points towards the air jets 42. The substrate 20 is arranged facing away from the air jets 42.

After having passed through the drying device 40, a dried intermediate laminate 32 is provided. This dried intermediate laminate 32 is transported with the aid of transport rollers 29 to laminating rollers 45 and 45'. The laminating roller 45 has a rotation direction $R_4$, wherein the laminating roller 45 rotates in a clockwise direction. The laminating roller 45' has the rotation direction $R_5$, this rotation direction $R_5$ being anticlockwise in the shown example. $R_4$ and $R_5$ therefore do not have the same rotation direction.

After having passed through the laminating rollers 45 and 45', a dried and strengthened intermediate laminate, i.e. the active substance laminate 33, is thus provided. This dried active substance laminate 33 may be rolled up, and therefore a rolled-up active substance laminate 34 may be provided.

An oral active substance laminate 100 according to the invention is shown in section in FIG. 4.

A carrier film 50 can be seen, however this is merely a part of the oral active substance laminate 100 in an intermediate step of the method according to the invention. The end product does not have a carrier film 50.

The substrate 20 is formed by two active-substance-free layers, specifically the first active-substance-free layer 61 and the second active-substance-free layer 62. The underside of the first active-substance-free layer 61 forms the underside 22 of the substrate 20. The upper side of the second active-substance-free layer 62 forms the upper side 21 of the substrate 20. Alternatively, the substrate 20 might also be formed by active-substance-containing layers. Furthermore, the substrate 20 might be formed by at least one active-substance-containing layer and at least one active-substance-free layer.

An active-substance-containing layer 31 is applied to the upper side 21 of the substrate 20.

The active substance of the active-substance-containing layer 31 may be an analgesic, especially fentanyl and/or buprenorphine, which especially is present as a base or as a salt, and/or oploid antagonist, especially naloxone. The active-substance-free layers 61 and 62, by contrast, may be formed from a polymer and/or a material that swells upon contact with water and/or a water-soluble material.

The active-substance-containing layer 31 for example has an areal density of 60 $g/m^2$. The active-substance-free substrate layers 61 and 62 by contrast each have an areal density of 120 $g/m^2$-140 $g/m^2$.

LIST OF REFERENCE SIGNS 10 product
11 carrier film
12 matrix
13 surface
14 underside
15 droplet
20, 20' substrate
21, 21' upper side
22, 22' underside
23, 23' container
24, 24' active-substance-containing mass
25, 25' gap
26, 26' first rotating roller
27, 27' second rotating roller
28 third rotating roller
28' transport roller
29, 29' transport roller
30, 30' intermediate laminate
31 active-substance-containing layer
32 dried intermediate laminate
33 active substance laminate
34 unrolled active substance laminate
40 drying device
41 drying zone
42 air jet
45, 45' laminating roller
50 carrier film
61 first layer of the substrate
62 second layer of the substrate
100 oral active substance laminate
$R_1$ rotation direction of the first roller
$R_2$ rotation direction of the second roller
$R_3$ rotation direction of the third roller
$R_4$ rotation direction of the laminating roller 45
$R_5$ rotation direction of the laminating roller 45'

The invention claimed is:

1. A method for producing an active substance laminate, having at least one active-substance-containing layer, which is arranged on a substrate, wherein the method comprises the following steps:
   a) providing a substrate having an upper side and an under side;
   b) applying an active-substance-containing mass in a gap formed by a first rotating roller and a second rotating roller, wherein the gap between the first rotating, roller and the second rotating roller has a width of from 0.2 mm-0.9 mm;
   c) transporting the substrate to the second roller by means of a third rotating roller in such a way that the active-substance-containing mass is applied to the upper side of the substrate in the form of an active-substance-containing layer to form an intermediate laminate by the second roller, wherein the rotation speed of the first rotating roller is 0.1 m/min-0.5 m/min, the rotation speed of the second rotating roller is 0.8 m/min-2.3 m/min and the rotation speed of the third rotating roller is 0.5 m/min-1.5 m/min, wherein the second roller has a rotation speed greater than the rotation speed of the third roller;
   d) transporting the intermediate laminate, formed by the substrate and the active-substance-containing layer, to a drying device;
   e) drying the active-substance-containing layer of the intermediate laminate in the drying device at a temperature of 30-120° C.; and
   f) guiding the dried intermediate laminate through laminating rollers and forming the active substance laminate.

2. The method according to claim 1, wherein the underside of the substrate is releasably connected, to a carrier film.

3. The method according to claim 1, wherein solvent is removed as the active-substance-containing layer is dried.

4. The method according to claim 1, wherein the substrate is free from an active substance or contains an active substance.

5. The method according to claim 1, wherein the substrate is formed by at least two active-substance-free layers.

6. The method according to claim 1, wherein the first roller, the second roller and the third roller rotate in the same rotation direction.

7. The method according to claim 1, wherein said drying is carried out in a plurality of drying zones having different temperatures by means of an air jet.

8. The method according to claim 1, further comprising:
   g) rolling up the active substance laminate.

9. The method according to claim 2, further comprising:
   h) unrolling the active substance laminate;
   i) optionally removing the carrier film; and
   j) dividing the active substance laminate into multiple active substance laminate portions.

* * * * *